(12) United States Patent
Ishihara et al.

(10) Patent No.: US 8,921,057 B2
(45) Date of Patent: Dec. 30, 2014

(54) METHOD OF ASSESSING PROPERTIES OF MAMMALIAN CELLS, AND METHOD OF DIAGNOSING CANCER USING THE SAME

(75) Inventors: Hideki Ishihara, Miki (JP); Tomoko Matsushima, Kobe (JP); Yuko Kawasaki, Kobe (JP)

(73) Assignee: Sysmex Corporation, Hyogo (JP)

(*) Notice: Subject to any disclaimer, the term of this patent is extended or adjusted under 35 U.S.C. 154(b) by 1341 days.

(21) Appl. No.: 11/597,414

(22) PCT Filed: May 30, 2005

(86) PCT No.: PCT/JP2005/009847
§ 371 (c)(1),
(2), (4) Date: Nov. 22, 2006

(87) PCT Pub. No.: WO2005/116241
PCT Pub. Date: Dec. 8, 2005

(65) Prior Publication Data
US 2007/0231837 A1    Oct. 4, 2007

(30) Foreign Application Priority Data

May 31, 2004  (JP) ................................ 2004-160389
Dec. 27, 2004  (JP) ................................ 2004-375639

(51) Int. Cl.
*G01N 33/574* (2006.01)
*C12Q 1/48* (2006.01)
*G01N 33/50* (2006.01)

(52) U.S. Cl.
CPC ............ *C12Q 1/485* (2013.01); *G01N 33/5011* (2013.01); *G01N 33/574* (2013.01)
USPC ...................................................... 435/7.23

(58) Field of Classification Search
CPC .............................. C12Q 1/485; G01N 33/574
See application file for complete search history.

(56) References Cited

U.S. PATENT DOCUMENTS

| | | | |
|---|---|---|---|
| 6,709,832 B1 | 3/2004 | Von Knebel Doeberitz et al. |
| 2002/0164673 A1 | 11/2002 | Ishihara et al. |
| 2003/0152993 A1 | 8/2003 | Doeberitz et al. |
| 2004/0023288 A1 | 2/2004 | Ridder et al. |

FOREIGN PATENT DOCUMENTS

| | | |
|---|---|---|
| EP | 1 600 513 A1 | 11/2005 |
| JP | 11-166031 A | 6/1999 |
| JP | 11-166931 | 6/1999 |
| JP | 2000-504683 | * 2/2002 |
| JP | 2002-519681 | * 7/2002 |
| JP | 2002-335997 A | 11/2002 |
| WO | WO 99/42821 A2 | 8/1999 |
| WO | WO 00/01845 A2 | 1/2000 |

OTHER PUBLICATIONS

Stites et al (Medical Immunology, 9th Ed, Appleton and Lange, 1997, pp. 250-251).*
Taber's Cyclopedic Medical Dictionary (1985, F.A. Davis Company, Philadelphia, p. 274).*
Busken, C et al, (Digestive Disease Week Abstracts and Itinerary Planner, 2003, abstract No. 850).*
Kaiser (Science, 2006, 313: 1370).*
Tockman et al (Cancer Res., 1992, 52:2711s-2718s).*
Alberts et al. (Molecular Biology of the Cell, www.garlandscience.com 2002 Table 17-1).*
Krontiris and Capizzi (Internal Medicine, 4th Edition, Editor-in-chief Jay Stein, Elsevier Science, 1994 Chapters 71-72, pp. 699-729).*
Pritzker (Clinical Chemistry, 2002, 48:1147-1150).*
Kim et al. (Annals of Oncology 2008 19:68-72).*
Boyd (The Basic Science of Oncology, 1992, McGraw-Hill, Inc., p. 379).*
Dorland's Medical dictionary for Healthcare Consumers (diagnose, Elsevier, www.mercksource.com, 2007).*
Dorland's Medical dictionary for Healthcare Consumers (risk, Elsevier, www.mercksource.com, 2007).*
Kim, J. H. et al, "*Amplified CDK2 and cdc2 activities in primary colorectal carcinoma*", Cancer, American Cancer Society, Philadelphia, PA, US, vol. 85, No. 3, Feb. 1, 1999, pp. 546-553, XP002979096.
Li, K. K. W. et al, "*Activation of cyclin-dependent kinases CDC2 and CDK2 in hepatocellular carcinoma*", Liver, Copenhagen, DK, vol. 22, 2002, pp. 259-268, XP002979097.
Ueno, Naoto T. et al, "*Cyclin-Dependent Kinase (CDK) Profiling to Predict Paclitaxel Chemosensitivity*", Proceedings of the Annual Meeting of the American Association for Cancer Research, New York, NY, US, vol. 46, Apr. 2005, p. 107, XP001536581.
Hideki, Ishihara et al, "*CDK Profiling Oif Gastriuntestunak Carcinoma Tissues*", Proceedings of the Annual Meeting of the American Association for Cancer Research, New York, NY, US, vol. 45, Mar. 2004, pp. 844-845, XP001536560.
Larry M. Weisenthal, et al, "Current Status of Cell Culture Drug Resistance Testing", (CCDRT), 2002, 14 Pages, http://weisenthal.org/oncol_t.htm.

(Continued)

*Primary Examiner* — Brad Duffy
*Assistant Examiner* — Nelson B Moseley, II
(74) *Attorney, Agent, or Firm* — Sughrue Mion, PLLC

(57) ABSTRACT

A CDK profile including a ratio of specific activities of two cyclin dependent kinases closely correlates with the malignancy grade and the presence/absence of the sensitivity to an irritant such as an anticancer agent of a cancer tissue in clinical medicine. Therefore, the properties of a mammalian cell, such as malignancy grade, proliferation potency, sensitivity to an irritant such as an anticancer agent can be assessed based on its CDK profile or by comparing the result of a specific activity ratio of two CDKs with a predetermined threshold corresponding to the ratio. This sensitivity assessing method shows a high ratio of correct assessing results particularly in positive or sensitivity and is useful in predicting efficacy of chemotherapy using the anticancer agent.

7 Claims, 7 Drawing Sheets

(56) References Cited

OTHER PUBLICATIONS

Ueno et al, "Predicting Paclitaxel Sensitivity by Functionality of the Spindle Assembly Checkpoint", Pro. Am. Assoc. Cancer Res., 46:107 (2005), Abstract-Poster Session I, S75, Abstract 1100.

M. Castedo, et al.;Cyclin-dependent kinase-1: linking apoptosis to cell cycle and mitotic catastrophe; Cell Death and Differentiation (2002), vol. 9, pp: 1287-1293.

K. J. Sweeney, et al; Cyclin D2 activates Cdk2 in preference to Cdk4 in human breast epithelial cells; Oncogene, 1997, vol. 14, pp. 1329-1340.

T. Nomoto, et al; Cell Cycle Regulation by Anti-Cancer Drugs, 1995, vol. 22, No. 12, pp. 1719-1723.

* cited by examiner (a) KATO III (b) K562

(c) Colo205

(d) HeLa (e) MCF7

(f) SKBr-3

(g) SW480

(h) T47D

METHOD OF ASSESSING PROPERTIES OF MAMMALIAN CELLS, AND METHOD OF DIAGNOSING CANCER USING THE SAME

FIELD OF THE INVENTION

This invention relates to a method of assessing malignancy grade of cancer and tumor, and sensitivity to irritants such as anticancer agents based on a ratio of activity value versus expression level of a cyclin dependent kinase (CDK) such as a CDK specific activity, and to a method of diagnosing cancer with use of the assessment method.

BACKGROUND ART

There are known a serum diagnosis of identifying a tumor marker in blood serum, a tissue diagnosis by biopsy, and a cytodiagnosis, as examples of the cancer diagnoses currently practiced at clinical places.

The tumor marker is a substance such as a protein, a glycoprotein, or a lipid, which is a product in a tumor cell as a result of expression of a gene that is no longer expressed in a process of generation or growth of an individual organism. The serum diagnosis is an assessment on a disease stage or malignancy grade of a tumor by detection of the tumor marker. Most of the currently available tumor markers, however, do not have high cancer specificity. Also, since the expression level of the tumor marker is very low in an early stage cancer, diagnosis accuracy is relatively low. For the above reasons, in the current medical institutes, reliability on cancer diagnosis using the tumor marker is not so high.

The tissue diagnosis and the cytodiagnosis are diagnostic methods, wherein after staining tissue or cell specimens obtained by biopsy, pathologists and cell screeners make an assessment on the stained specimens based on the conditions or stained patterns of the specimens through microscopic observation, based on their own medical or clinical experiences. The staining methods are different among the medical institutes. Also, the final assessment depends on medical or clinical experiences of pathologists or cell screeners. Accordingly, it is difficult to make a definite diagnosis in a delicate stage such as a moderately differentiated stage or stage 1. In a worse case, selection on medication treatment may be erred, thereby leading to serious progression of a cancer.

In view of the above, the TNM classification, as a criterion for standardizing the diagnostic methods, has been established, and globally been spread. The TNM classification for a cancer is a criterion adopted by the Union International Contre Cancer (UICC), and shows progress levels of malignant tumors. "T" represents the size of a primary tumor, "N" represents the level of a lymph node metastasis, and "M" represents a distant metastasis. "T" is classified from level "1" indicating that the tumor is localized within the tissue to level "4" indicating that tumorigenesis appears in a site other than the affected tissue. "N" is classified from level "0" indicating that no local lymph node metastasis is observed to level "3" indicating that a lymph node metastasis is histopathologically observed. "M" is classified from level "0" indicating that no distant metastasis is observed to level "1" that a distant metastasis is observed. In any of the parameters of "T", "N", and "M", the larger the numerical value is, the poorer the prognosis is, which means that the malignancy grade of the cancer is high.

The TMN (sic, correctly TNM) classification is generally used because it is useful for determination of a treatment method, or prognosis assessment. However, even if patients are diagnosed to be in an early stage of a cancer according to the TNM classification, in the case of a breast cancer, relapse by a distant metastasis is observed in about 10 to 20% of the patients within 5 years after the diagnosis, leading to death, which is a clinically important matter. Although the assessment based on the TNM classification is useful for medical staffs to grasp clinical conditions of patients at the time of diagnosis, the assessment has not successfully led to accurate prediction on a prognosis.

In addition to the above diagnostic method, there is proposed a method of diagnosing malignancy grade of a cancer by measuring the DNA content of cancer cells, using a fluorescence-activated cell sorter (FACS), and based on the measurement result, in light of a point that a cancer tissue contains a large amount of polyploids such as triploids or tetraploids. However, it is required to disperse an obtained biopsy specimen into single cells in order to measure the biopsy specimen by the FACS. It is generally not easy to disperse a biopsy specimen into single cells, and a high level skill is required to do this. For the above reasons, application of the cancer diagnostic method using the FACS in the current medical institutes is reportedly difficult.

Under the foregoing circumstances, there is a need of establishing a diagnostic method capable of providing a definite diagnosis without the need of a cumbersome preparation of samples, namely, dispersion into single cells, and with less variation in diagnosis resulting from individual assessments or different assessment methods in medical institutes at clinical places.

In recent years, there is expected a molecular diagnosis using an apparatus, as a standardized cancer diagnostic method with less variation in diagnosis by diagnosticians. One of the molecular diagnoses is a method of assessing malignancy grade of cancer, using a DNA chip, based on a comparison result on expression of gene transcript between a biopsy specimen and a standard specimen. However, the expression of gene transcript does not have a high correlation to produced proteins in a living organism. Accordingly, effectiveness of the diagnostic method is thought to be less trustworthy in the clinical places.

Development and study have been progressed concerning a molecular diagnosis based on a protein which is expressed in a living organism. For instance, D1 proposes a diagnostic method, wherein expression levels of CDK1 and CDK4 in a sample, and mutation of p53 according to needs, are used as indicators. D2 proposes a diagnostic method of a cancer and precancerous states, using overexpression of CDK4, CDK6, or cyclin dependent kinase inhibitor (CDK inhibitor).

It is known that expression of cyclin dependent kinase (CDK) is high in a cell where proliferation is induced by a growth factor. Generally, however, a certain amount of CDK exists in a cell, and the CDK shows its activity in a specific stage of a cell cycle depending on the kind of CDK, by binding to cyclin molecules under activation of phosphorylation or a like action, and forming a complex of CDK and cyclin. Also, it is known that the CDK inhibitor is bound to CDK and/or a complex of cyclin and CDK, thereby inhibiting the CDK activity. As mentioned above, since the actual cell cycle is complicatedly controlled, the assessment simply based on the expression level of CDK, cyclin, or CDK inhibitor does not provide a sufficient indicator for a controlled state of the cell cycle.

D3 discloses a diagnostic method of using CDK activities as an indicator for assessing malignancy grade of cancer, considering binding to cyclin, or influence of an inhibitor, and a method of measuring CDK activities without using a radioactive substance. However, data concerning the CDK activities to be measured by the disclosed method fails to provide diagnosis precision sufficient as a substitute of the cancer diagnoses currently practiced at the clinical places.

It is sometimes required to know sensitivity of tumor cells in vitro to an anticancer agent, as an indicator on effectiveness of a chemotherapy using the anticancer agent. Examples of the known in vitro tests of measuring sensitivity of tumor cells to agents such as an anticancer agent are MTT assay method and DISC method. The MTT assay method is a method, utilizing a phenomenon that MTT (3-(4,5-dimethylthiazole-2-yl)-2,5-diphenyltetrazolium bromide) can be cleaved by a reductase (succinate dehydrogenase) in mitochondria when the MTT is trapped in a living cell, but that the MTT cannot be cleaved when trapped in a dead cell. The MTT assay method comprises cultivating a cancer cell for 3 hours by addition of the MTT and an agent to be measured, measuring light absorbency i.e. succinate dehydrogenase activity, and quantitatively determining the number of living cells. It is reported that 80% of assessment prediction results by the in vitro assessment method accorded with relapse or no relapse by an actual chemotherapy using an anticancer agent, and that 68% of prediction positive i.e. sensitive to the anticancer agent by the in vitro assessment method showed no relapse by the actual chemotherapy using the anticancer agent (see D4).

DISC method is a method comprising contacting a cancer cell with an anticancer agent for 4 days, staining the dead cells with a fast green, identifying the living cells by staining the living cells with hematoxylin-eosin to assess whether the cancer cell is dead or alive. It is reported that a probability i.e. a matching rate between in vitro results and actual results is 82.7%, and a probability on positive prediction rate is 62.5% (see D4).

In any of the above methods, the positive prediction rate is less than 70%, which is an insufficient indicator for determining whether a chemotherapy using an anticancer agent is to be started.

D1: JP patent publication No. 2002-504683
D2: JP patent publication No. 2002-519681
D3: JP patent publication No. 2002-335997
D4: Weisenthal, L. M. and Nygren. P (2002) Current status of cell culture drug resistance testing(CCDRT), http://weisenthal.org/oncol_t.htm

DISCLOSURE OF THE INVENTION

In view of the above, it is an object of the invention to provide a method that enables to assess malignancy grade i.e. metastasis likelihood, relapse likelihood, and prognosis estimation, of cancer tissues in clinical medicine, and also enables to accurately and stably make an assessment while suppressing variation in diagnosis by medical institutes or individual clinicians, and a molecular diagnostic method of a cancer using the assessment method.

It is another object of the invention to provide an assessment method with a higher precision, as compared with a conventional chemotherapy sensitivity test using a pharmaceutical agent, which enables to utilize an assessment result on sensitivity of mammalian cells to an irritant such as an anticancer agent, as an indicator for determining whether a chemotherapy such as a treatment using an anticancer agent is to be started.

As a result of extensive research and study concerning a relationship between specific activity of cyclin dependent kinase and pathological assessment on tissues, the inventors found that there is a high correlation between a CDK profile including specific activities of two kinds of cyclin dependent kinases (CDKs) or inverse numbers thereof, and cell proliferation potency and tissue malignancy grade i.e. relapse likelihood. Thus, the inventors accomplished the inventive property assessment method. They also found a correlation between the CDK profile concerning two CDKs and sensitivity of mammalian cells to an irritant, and accomplished the inventive sensitivity assessment method.

A method of assessing a property of a mammalian cell of the present invention comprises assessing a property of a mammalian cell based on a profile concerning cyclin dependent kinase of the cell (hereinafter, referred to as "CDK profile" of the cell) including a ratio of activity value versus expression level of a first CDK contained in the cell and a ratio of activity value versus expression level of a second CDK contained in the cell.

The property may be assessed by comparing the CDK profile of the cell with a CDK profile of a standard mammalian cell.

In one embodiment of the assessing property method, the assessing step may be carried out by comparing a ratio of A1 versus A2 with a threshold value corresponding to the ratio, wherein A1 is a ratio of activity value versus expression level of a first CDK contained in the cell and A2 is a ratio of activity value versus expression level of a second CDK contained in the cell.

The CDK used in the inventive method is preferable to be selected from the group consisting of CDK1, CDK2, CDK4, CDK6, cyclin A dependent kinase, cyclin B dependent kinase, and cyclin D dependent kinase. More preferably, the first CDK is CDK1, and the second CDK is CDK2.

The property may include proliferation potency and malignancy grade of the mammalian cell.

The malignancy grade may include metastasis likelihood, relapse likelihood and prognosis estimation. The metastasis may include lymph node metastasis and distant metastasis.

A method of diagnosing cancer of the invention comprises diagnosing malignancy grade of a cell obtained from a living organism with use of the aforementioned assessing property method of a mammalian cell.

In another aspect of the invention, a method of assessing sensitivity of a mammalian cell to an irritant comprises assessing sensitivity of a mammalian cell based on a CDK profile of the cell including a ratio of activity value versus expression level of a first CDK contained in the cell and a ratio of activity value versus expression level of a second CDK contained in the cell.

In one embodiment of the assessing sensitivity method, the assessing step may be carried out by comparing a ratio of A1 versus A2 with a threshold value corresponding to the ratio, wherein A1 is a ratio of activity value versus expression level of a first CDK contained in the cell and A2 is a ratio of activity value versus expression level of a second CDK contained in the cell.

In a preferable embodiment, the inventive method of assessing a sensitivity further comprises comparing A1 and/or A2 with a threshold value corresponding to A1 and A2 respectively.

The CDK is preferable to be selected from the group consisting of CDK1, CDK2, CDK4, CDK6, cyclin A dependent kinase, cyclin B dependent kinase, and cyclin D dependent kinase.

The irritant is preferable to be selected from the group consisting of growth factor, anticancer agent, and mutagen.

"Profile concerning CDK" or "CDK profile" in the specification and claims of the application means information containing a ratio of activity value versus expression level such as specific activity of at least one kind of CDK and/or a value calculated using activity values and expression levels of two or more kinds of CDKs contained in a cell. The examples of the value include a ratio of A1 versus A2, i.e. A1/A2 or A2/A1, wherein A1 is a ratio of activity value versus expression level of a first CDK and A2 is a ratio of activity versus expression level of a second CDK.

"Specific activity of CDK" or "CDK specific activity" used herein means kinase activity of predetermined amount, which is calculated by the following equation.

CDK specific activity=(activity value of CDK)/(expression level of CDK) In the above equation, the activity value of CDK corresponds to a unit based on an amount of phospholylated substrate and is a value as relative activity value calculated with activity values of a standard cell and a cell contained in the specimen. The expression level of CDK is an amount (a unit of the number of molecules) of CDK contained in the cell.

"Metastasis likelihood" in the specification and claims of the application is a degree of probability with which a cancer cell may move from a primary tumor to a distant tissue, resulting in development of metastasis. It is known that cancer cells with a high degree of probability i.e. cells with a high metastasis likelihood have biological characteristics shown by way of infiltration capability or migration capability.

"Relapse likelihood" is a frequency of relapse in cancer patients who are classified according to a certain classification e.g. a classification based on stages. For instance, stage III corresponds to a relapse rate of 50%, which indicates a higher relapse probability than stage II corresponding to a relapse rate of 20%.

"Prognosis estimation" is a frequency of death of cancer patients within 5 or 10 years after the diagnosis, who are classified according to a certain classification e.g. a classification based on stages. For instance, stage III corresponds to a death rate of 50%, which indicates more deaths than stage II corresponding to a death rate of 20%, and indicates that the prognosis is poor.

EFFECT OF THE INVENTION

The method of assessing properties of mammalian cells according to the invention enables to eliminate measurement errors or variations resulting from preparation methods of samples for measurement because a specific activity is used as an indicator. Also, a CDK specific activity profile, which is used as an assessment indicator in the invention, utilizing specific activities of two kinds of CDKs, particularly, a ratio of the specific activities of the two kinds of CDKs, has a high correlation to a property of cancer cells such as aneuploidy or a ratio of cells under a normal cell cycle. Use of the CDK profiles enables to provide a molecular diagnosis with a high reliability. Also, the inventive method uses the indicator based on the cell cycle. This enables to make an assessment not only on biological characters and properties of cells but also on clinical characters such as malignancy, as well as sensitivity or resistance against pharmaceutical agents such as anticancer agents, or external irritants. Particularly, the inventive method is advantageous in providing an indicator for determining whether a chemotherapy using an anticancer agent is to be started, because the inventive method provides a high probability on prediction positive or sensitive to the anticancer agent.

BEST MODE FOR CARRYING OUT THE INVENTION

Figure 1:
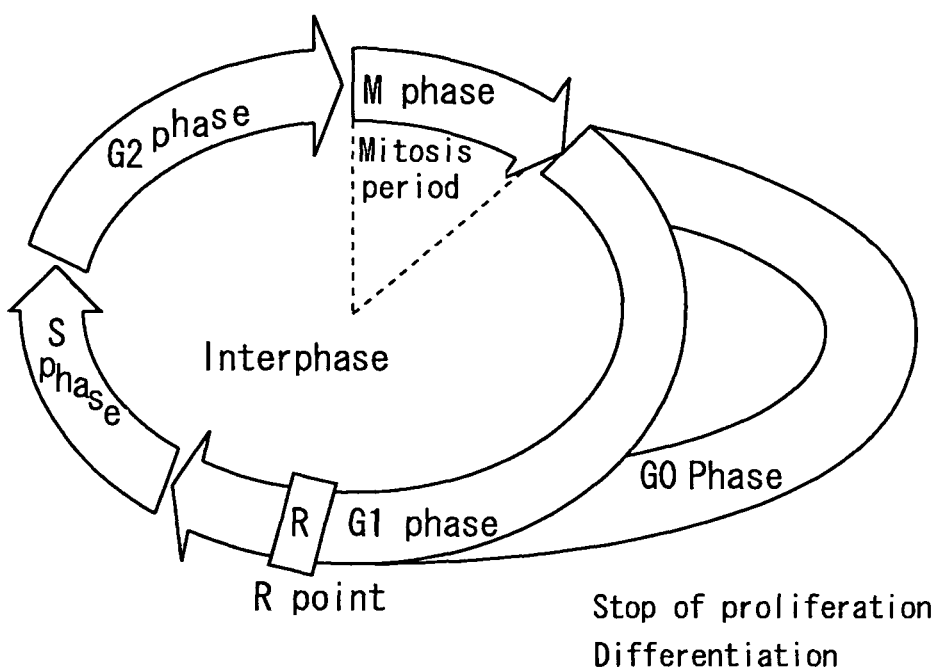
FIG. 1 is a diagram for explaining a cell cycle.
Figure 2:
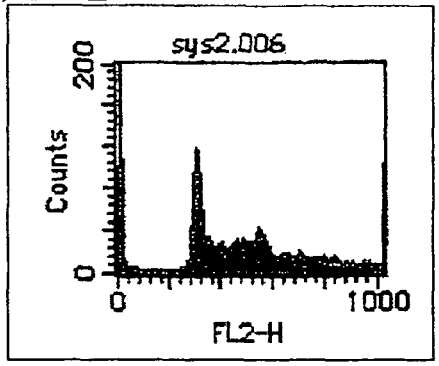
FIGS. 2(a) through 2(h) are diagrams showing measurement results on the DNA content in various cell lines.
Figure 2:
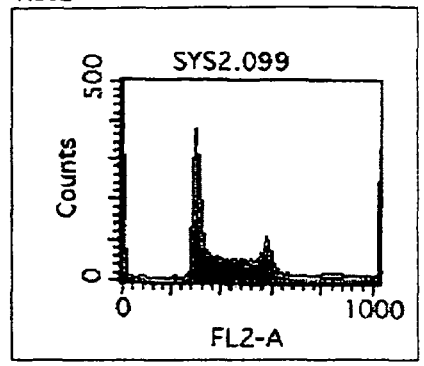
Figure 2:
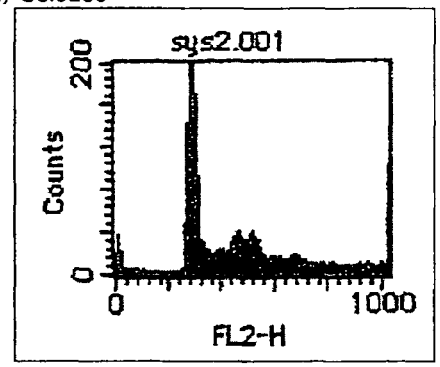
Figure 2:
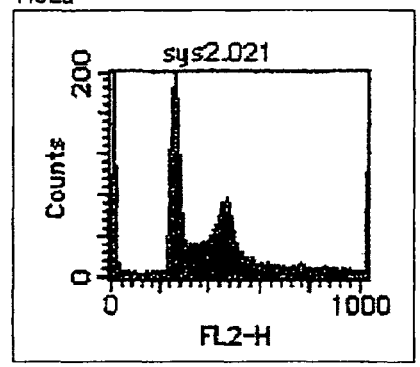
Figure 2:
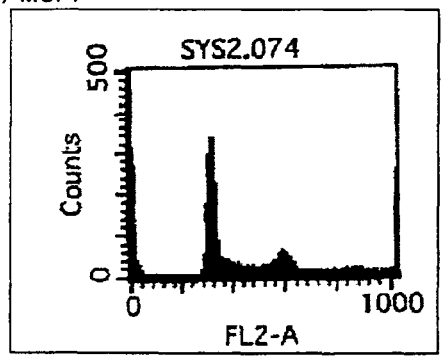
Figure 2:
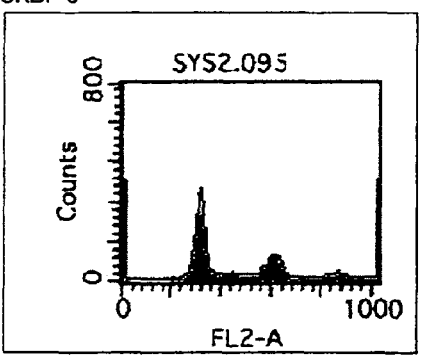
Figure 2:
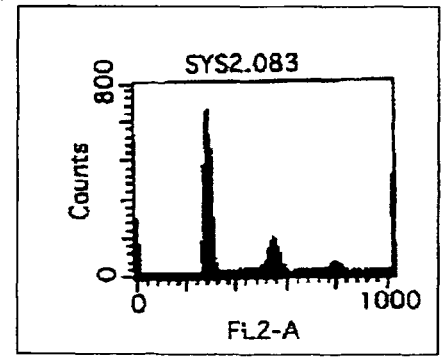
Figure 2:
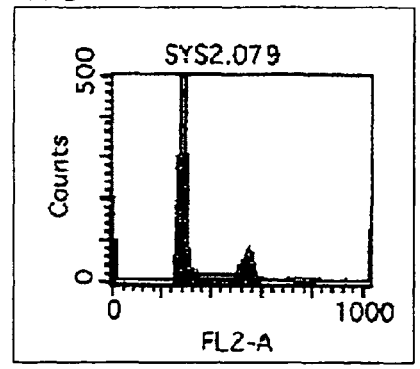

A method of assessing a property of a mammalian cell of the present invention comprises assessing a property of a mammalian cell based on a CDK profile including a ratio of activity value versus expression level of a first CDK contained in the cell and a ratio of activity value versus expression level of a second CDK in the cell. Application of the inventive method to a tissue containing a tumor cell makes it possible to provide properties of a tumor cell and support diagnosis of malignancy grade of cancer.

The mammal such as, but not limited to, human, particularly human who is required to assess the clinical condition, more particularly a patient required to assess the cancerous stage, is applicable for the method of the present invention.

Cells to be assessed by the invention may include cells constituting a tissue of living body of the mammal. The tissue includes supporting tissue such as fibrous connective tissue, cartilage tissue, bone tissue, blood and lymph; epithelium tissue; muscle tissue; and nervous tissue. Particularly, the preferable cell is a cell required to obtain clinical information, such as a cancer cell derived from the tissue which dysfunctions in growth regulation and results in breaking a balance in an individual. Preferable examples of the cancer cell include a cell derived from a tumor generated in organs such as breast, lung, liver, stomach, colon, pancreas, skin, uterus, testis, thyroid gland, parathyroid gland, lymphatic system, and bone marrow.

These cancer cells may be cells obtained directly from the targeted tissue of the living body; cells obtained from excretion of the individual, such as urine and sputum; or cells subcultured. In the case of obtaining information with respect to cancer, cells obtained from the tumor tissue are preferably used.

The property of a mammalian cell to be assessed may include proliferation potency and malignancy grade of the cell. The proliferation potency means activity level in cell number growth, and may include information whether the cell proliferation is under abnormal process of cell cycle or not, i.e. the cell is cancerous or not, and information with respect to aneuploidy and so on. The malignancy grade of the cell includes, for instance, metastasis likelihood, relapse likelihood, prognosis estimation and so on.

"Relapse" include a case that the same kind tumor as one eliminated by surgery of extirpating a part of the organ appears again in the remained part of the organ after the surgery, and a case of metastasis relapse wherein a cancerous cell migrates from a primary tumor to a distant tissue or distant organ and proliferates autonomically in the distant tissue or organ. The case where relapse is observed within 5 years is generally regarded as a case of "high relapse likelihood". Stage III corresponding to a relapse rate of 50% indicates a higher relapse than stage II corresponding to a relapse rate of 20%. Prognosis means prediction of course of disease and death due to disease. The higher the frequency of death within 5 or 10 years is, the worse the prognosis estimation is. For instance, stage III corresponds to a death rate of 50%, which indicates poorer prognosis than stage II corresponding to a death ratio of 20%.

The cyclin dependent kinase (CDK) is a generic term for various enzymes which are activated by binding to cyclin. The CDK acts in a specific phase of a cell cycle depending on its kind. The CDK inhibitor is a generic term for factors which can inhibit the CDK activity by binding to a complex of cyclin and CDK.

The cell cycle is divided into four phases: G1 phase, S phase, G2 phase, and M phase, as shown in FIG. 1. Referring to FIG. 1, a cell starts its proliferation, and then undergoes various events such as DNA replication, chromosome distribution, nuclear division, and cytokinesis, and returns to the starting point as two daughter cells. S phase is a period of DNA replication. M phase is a mitosis period. G1 phase is a period after completion of the mitosis and before start of DNA synthesis, and is a preparatory checking period before the cell enters M phase. When the cell passes a checkpoint (in the case of an mammalian cell, R point) in G1 phase, the cell cycle starts, and normally the cell cycle completes without stopping at any point in the cycle. G2 phase is a period after completion of DNA synthesis and before start of mitosis. Primary checkpoints in the cell cycle are the point of time immediately before the cell enters S phase after passing G1 phase, and the point of time when the cell directs toward mitosis after passing G2 phase. Particularly, the checkpoint in G1 phase is important because the checkpoint causes start of S phase. After the cell passes a certain point in G1 phase, the cell cycle progresses from S phase to G2 phase, M phase, and then to G1 phase without stopping the proliferation, even after a proliferation signal disappears. A cell in a rest period i.e. G0 period, which is out of the cell cycle, carries the DNA content in G1 phase, and its proliferation is suspended. The cell in G0 phase can return to S phase in the cell cycle by proliferation induction, after staying for a relatively longer time comparing with the period of G1 phase.

The cyclin dependent kinase (CDK) may be preferably to be selected the group consisting of CDK1, CDK2, CDK4, CDK6, a cyclin A-dependent kinase, a cyclin B-dependent kinase, and a cyclin D-dependent kinase. The cyclin A-dependent kinase represents a CDK that exhibits activity by binding to cyclin A. Currently known examples of the cyclin A-dependent kinase include CDK1 and CDK2. The cyclin B-dependent kinase represents a CDK that exhibits activity by binding to cyclin B. Currently known examples of the cyclin B-dependent kinase include CDK1. The cyclin D-dependent kinase represents a CDK that exhibits activity by binding to cyclin D. Currently known examples of the cyclin B-dependent kinase include CDK4 and CDK6.

Each of these CDKs binds to a specific cyclin as shown in Table 1, and forms the cyclin-CDK complex (hereinafter, sometimes called as "activated CDK"), and acts in a specific phase of the cell cycle as shown in Table 1. For instance, CDK1 binds to cyclin A or cyclin B and become an activated form, CDK2 binds to cyclin A or cyclin and become an activated form, each of CDK4 and CDK6 binds to cyclin D1, D2, or D3 and become an activated form. On the other hand, such CDK activation may be inhibited by CDK inhibitor as shown in Table 1. For instance, p21 inhibits activation of CDK1 and CDK2, p27 inhibits activation of CDK2, CDK4 and CDK6, and p16 inhibits activation of CDK4 and CDK6.

TABLE 1

| CDK | Cyclin to be bound | CDK inhibitor to be bound | Relating phase of activated CDK |
|---|---|---|---|
| CDK4 | Cyclin D1 | p27, p16 | G1 |
| CDK6 | Cyclin D2 | | |
| | Cyclin D3 | | |
| CDK2 | Cyclin E | p27 | G1 → S proceeding |
| CDK2 | Cyclin A | p21, p27 | Activation of S phase |
| CDK1 | Cyclin A | p21 | G2 → M proceeding |
| | Cyclin B | | |
| Cyclin A-dependent kinase | Cyclin A | p21, p27 | CDK1: G2 → M CDK2: mid period of S phase |
| Cyclin B-depedent kinase | Cyclin B | p21 | CDK1: G2 → M |
| Cyclin D-dependent kinase | Cyclin D | p27, p16 | CDK4, 6: G1 |

The CDK profile used in the invention may be obtained by measuring expression levels and activity values of two or more kinds of CDKs out of the above mentioned CDKs, and calculating a ratio of expression level versus activity value of CDK, i.e. CDK specific activity represented in the following formula or inverse number thereof, with respect to each of the measured CDKs.

CDK specific activity=(CDK activity value)/(CDK expression level)

Accordingly, the specific examples of CDK profiles include a profile including CDK specific activity (called as "CDK specific activity profile"), and a profile including an inverse number of CDK specific activity (called as "CDK specific activity inverse number profile"), and so on.

The CDK activity value represents kinase activity level which is measured as an amount of the substrate phospholylated by binding to a specific cyclin with a conventional method for measuring enzymatic activity. The measured value is expressed by U. Examples of the substance include histone 1(H1) upon which an activated CDK1 or activated CDK2, Retinoblastoma protein upon which an activated CDK4 or activated CDK6. Specifically, there is proposed a process comprising steps of preparing a sample containing activated CDK from a cell lysate as a specimen; labeling a substrate with $^{32}$P by reacting with $^{32}$P-labeled ATP ($\gamma$-[$^{32}$P]-ATP) on the activated CDK; measuring the phosphoric acid amount in the labeled substrate; and quantitatively determining the amount of the labeled substrate, based on a standard curve pre-created using a standard sample. Also, Japanese Unexamined Patent Publication No. 2002-335997 discloses a process without using a radioactive substance as a label. The disclosed process comprises steps of preparing a sample containing activated CDK of interest from a cell lysate as a specimen; reacting the substrate in the sample with adenosine 5'-O-(3-thiotriphosphate) (ATP-$\gamma$S); introducing monothiophosphate into serine or threonine residue in the substrate; labeling the substrate by binding a fluorescent substance or a labeled enzyme to a sulfur atom in the introduced monothiophosphate; measuring the amount of the labeled thiophosphorylated substrate (or the amount of the fluorescent substance in the case where the fluorescent substance is used); and quantitatively determining the phosphoric acid amount in the sample based on a standard curve pre-created using a standard sample.

Samples for measuring the CDK activity are prepared by collecting CDK of interest from cell lysates as specimens. The preparation may be performed by using an anti-CDK antibody specific to CDK of interest. In the case where the activity of a specific cyclin dependent kinase e.g. a cyclin A-dependent kinase, a cyclin B-dependent kinase, or a cyclin E-dependent kinase is measured, the preparation may be performed by using an anti-cyclin antibody specific to the cyclin depended by the kinase of interest. In both of the case with use of the anti-CDK antibody and the case with use of the anti-cyclin antibody, the samples to be measured contain CDK other than the activated CDK. For instance, the sample may contain a CDK complex in which CDK inhibitor binds to cyclin-CDK complex. Also, when the anti-CDK antibody is used, the sample may contain not only CDK itself, but also various CDK complexes such as CDK-cyclin complex, CDK-CDK inhibitor complex, CDK-cyclin-CDK inhibitor complex, or complexes of CDK and other compounds. In view of this, CDK activity is measured in terms of the unit (U) of the phosphorylated substrate under the condition that various CDKs such as activated CDK, unactivated CDK, and various competitive reactive substances co-exist.

The CDK expression level is a relative amount of target CDK (unit corresponding to the number of molecules), which is contained in a cell lysate as a specimen, and can be measured by a conventional known process of measuring the amount of a target protein in a protein-containing mixture. For example, an enzyme-linked immunosorbent assay (ELISA) or a Western blot process may be used. Also, a process disclosed in Japanese Unexamined Patent Publication No. 2003-130871 may be used. A target protein i.e. CDK can be bound by using an antibody specific to the target protein. For instance, use of an anti-CDK1-antibody enables to bind CDK1s, such as CDK1 itself, CDK1-cyclin complex, CDK1-CDK1 inhibitor complex, CDK1-cyclin-CDK1 inhibitor complex, and complexes of CDK1 and other compounds, in cells of the specimen.

Accordingly, the specific activity calculated by the above-mentioned formula corresponds to a ratio of CDK exhibiting enzymatic activities to the CDKs in the cells. The ratio can be regarded as CDK activity exhibited due to a proliferation condition inherent to mammalian cells to be assessed. A sample for measurement (sample solution containing cells), particularly, a sample prepared from specimen obtained by biopsy, is greatly affected by a sample preparation process and the amount of extracellular components, e.g. extracellular matrix contained in the tissues obtained by biopsy. However, the ratio of activity value versus expression level of CDK is not influenced by the sample preparation process. Accordingly, use of the ratio of activity value versus expression level of CDK is advantageous, because the ratio may highly correlate with clinical finding comparing with activity itself.

A CDK profile including specific activity or the inverse number thereof of two or more kinds of CDKs provides information relating to which CDK has the priority in its activity, thereby, it may further provide information about the ratio and/or the number of cells in each phase and information about which phase has the priority in the cell existing. Hereafter, a method of the present invention, mainly a method with use of CDK specific activity, will be described The kind of CDK whose specific activity is measured may be appropriately selected depending on kinds of properties required for assessment. Generally, since a cancer cell is out of normally controlled growth and proliferates rapidly, it is considered that the ratio of cells staying in the period of S phase and G2 phase may be large and such condition is canceration. The tumor containing cells under the abnormal condition may progress rapidly and be estimated at high grade in malignancy. And, the aneuploidity is considered to be caused by passing through an abnormal M phase, or proceeding to G1 phase and then S phase without undergoing M phase. Therefore, the specimen in which the ratio of cells in M phase is low may be estimated at high grade in malignancy. Accordingly, when CDK1 as a first CDK and CDK2 as a second CDK are selected, CDK2 specific activity is a value which reflects a ratio of cells in S phase in the specimen belonging to the group of specimens exhibiting similar CDK1 specific activities when classifying according to a degree of CDK 1 specific activity. The tissue containing a lot of cells staying in S phase may be estimated at high grade in malignancy in clinical medicine. In other words, the tissue tumor may be malignant having high metastasis likelihood and poor prognosis.

According to the invention, malignancy grade of a cell specimen may be assessed by predicting the ratio of cells in the specific phase of the cell cycle based on a CDK specific activity profile including specific activities of two or more kinds of CDKs considering the kind and known function of CDKs. Alternatively, malignancy grade of a cell specimen may be assessed by making a specific activity profile of two or more kinds of CDKs contained in a standard cell obtained from non-cancerous tissue corresponding to the tissue supplying the cell specimen, and comparing the CDK specific activity profile of the cell specimen with the pre-made CDK specific activity profile of the standard cell.

A preferable example of the CDK specific activity profile includes the ratio of the specific activity of two kinds of CDKs. In this case, the properties of the cell are assessed by comparing the ratio of the specific activities of two kinds of CDKs with a predetermined threshold value corresponding to the ratio.

A threshold value to be used in the inventive cell property assessment method is appropriately determined depending on the kinds of cells to be measured, and assessment items. The threshold value may be set by selecting a ratio value of specific activities serving as a borderline for an employed assessment item based on a database of multitudes of cell specimens and individuals relating to the employed assessment item, and a database of CDK specific activities of the employed cell specimens. For instance, a threshold value is determined as follows: a ratio of specific activity of one kind of CDK to specific activity of the other kind of CDK which is known to have a correlation to the one kind of CDK is obtained with respect to tumor cells obtained from patients whose cancerous malignancy grade has been assessed by pathologists; the obtained ratio values are ranked from the smallest value to the largest value; and then a median capable of classifying the patients into two equal groups is defined as the threshold value.

The inventive assessment method is not only applied to cell properties such as proliferation potency or malignancy grade, but also is applicable to cell sensitivity to an irritant. For instance, recently there is pointed out that a difference in effectiveness of pharmaceutical agents such as an anticancer agent due to genetic constitution of patients results from a difference in cell sensitivity to an irritant. In other words, the properties inherent to cells include a property as to whether the cells are sensitive to an irritant. The ratio of specific activities of two kinds of CDKs also has a correlation to the sensitivity to the irritant. In view of this, the inventive method of assessing sensitivity of mammalian cells includes the method of assessing cell sensitivity to an irritant, based on a CDK profile including a ratio of expression level versus activity value with respect to a first CDK, and a ratio of expression level versus activity value with respect to a second CDK. Examples of the CDK profile are a CDK specific activity profile including CDK specific activities, and a CDK specific activity inverse number profile including inverse numbers to the CDK specific activities. An exemplified embodiment using the CDK specific activity profile is directed to a method of assessing cell sensitivity to an irritant by comparing a predetermined threshold value with a ratio of a specific activity of a first CDK to a specific activity of a second CDK.

The irritant is selected from the group consisting of growth factors, anticancer agents, and mutagens. The contents to be assessed and the contents on sensitivity differ depending on the kinds of the irritants. For instance, effectiveness or non-effectiveness is assessed with respect to the anticancer agents, and responsiveness or non-responsiveness is assessed with respect to the mutagens or growth factors.

The threshold value serving as an assessment indicator in the inventive cell sensitivity assessment method is appropriately set depending on the kind of irritant. The threshold value is set by examining a correlation between specific activity values of CDK serving as assessment indicators for the cell specimens prepared in advance, and sensitivity/non-sensitivity of the cell specimens to an irritant, and by selecting a value in a boundary area between the sensitivity and non-sensitivity, as a threshold value. The threshold value may be set by classifying patients who are actually exposed to an irritant into a sensitivity group and a non-sensitivity group concerning an irritant sensitivity, based on ratios of specific activities of the two CDKs, which are measured independently of the irritant sensitivity test. Alternatively, the threshold value may be set by stimulating various cultured tumor cells with an irritant, measuring a proliferation level or a responsiveness level of the cells to the irritant, classifying the patients into a sensitivity group and a non-sensitivity group based on ratios of specific activities of the two kinds of CDKs, which are measured independently of the irritant sensitivity test.

There is a case that the ratio of the specific activities of the two CDKs is largely away from the threshold value because one or both of the CDK specific activities to be used in the assessment are unduly small or unduly large, depending on the kind of the cell to be measured or the kind of the irritant to be used. Also, there is a case that the CDK specific activity value itself as a measured item is unduly small if the measured cell is assessed to be non-sensitive to an irritant. In such a case, it is preferable not only to make an assessment merely based on the ratio of the specific activity values, but also to assess the irritant sensitivity, considering the largeness or smallness of the CDK specific activity values to be used in the assessment. Specifically, a threshold value as an assessment indicator is set with respect to the specific activity value itself, and an assessment is made, considering a comparison result regarding the actually measured specific activity value with the specific activity threshold value.

In the case where the CDK specific activity value and the corresponding threshold value are compared, and the ratio of the CDK specific activities and the corresponding threshold value are compared, respectively, to assess the irritant sensitivity, the comparison order is not specifically limited. It is preferable to determine the comparison order, according to needs, depending on the kinds of the irritants, or the kinds of the cells. For instance, the specific activity value may be compared with the corresponding threshold value to determine certain cells which are assessed to belong to a sensitivity group or a non-sensitivity group, and thereafter, the ratio of the specific activities may be compared with the corresponding threshold value with respect to the rest of the cells which have not been assessed. Alternatively, in the case where one or both of the specific activity values are unduly small or unduly large in the cells for measurement, first, the ratio of CDK specific activities may be compared with the corresponding threshold value to classify the cells into a sensitivity group and a non-sensitivity group. Thereafter, the specific activity value itself may be compared with the corresponding threshold value with respect to the cells in which one or both of the specific activity values are unduly large or unduly small to assess sensitivity again. Then, an assessment result based on the comparison result of the ratio of the specific activity values with the corresponding threshold value may be corrected based on the re-assessment.

The specific activity value is different depending on the CDK activity measurement method, the CDK expression level measurement method, the kinds of antibodies to be used in the measurement, or the like. Accordingly, it is necessary to make the specific activity measurement method in creating a database for setting the threshold value identical to the specific activity measurement method with respect to a cell to be assessed, as far as the assessment method based on a comparison result with the threshold value is employed in the inventive assessment method.

EXAMPLES

First, methods used in the following examples, i.e. a method for preparing samples for measurement and methods for measuring specific activity of CDK and expression level of CDK, are described.

[Preparation of Cell Lysate]

Tissues each having a volume of 2 $mm^3$ extirpated by biopsy or cultured cells of cancer cell lines as shown in Table 2 are used as specimens of organisms to be assessed.

TABLE 2

| Cultured cells | Kind of tumor |
| --- | --- |
| KATO-III | Gastric cancer |
| K562 | Leukemia |
| Colo205 | Colon cancer |
| HeLa | Cervical cancer |
| MCF-7 | Brest cancer |
| SW-480 | Colon cancer |
| SKBr | Brest cancer |
| T47D | Brest cancer |

The tissues and cultured cells were lysed with lysis buffer (0.1 w/v % nonidet-40P (NP40) (Calbiochem), 50 mM tris-HCl (pH:7.4), 5 mM EDTA, 50 mM sodium fluoride, 1 mM sodium orothovanadate, and 100 μl/ml Proteinase Inhibitor Cocktail (Sigma, St. Louis, Mo.)) by syringing 10 times with a syringe (allowable content: 5 ml) having a 23 G needle in ice bath to obtain cell solutions respectively. The concentration of the cell solution of the cultured cells was $1 \times 10^7$ cells/5 ml.

After centrifugation at 15000 rpm for 5 min at 4° C. to remove insoluble materials, the supernatants (cell lysates) were used for the following measurements.

[Measurement of CDK Activity]

Each of the cell lysates prepared by the aforementioned method was added to a lysis buffer in a 1.5 ml-Eppendorf so that 100 µg of protein in total amount was dissolved in 500 µl of the lysis buffer, and the resultant solution subjected to measurement of CDK activity.

To the solution for measurement, added were sepharose beads (Bio-Rad, Calif., U.S.A.) coated with 20 µl of Protein A and 2 µg of antibodies specific to a CDK whose activity was to be measured, i.e. polyclonal anti-CDK1-antibodies or polyclonal anti-CDK2-antibodies (Santa Cruz Biotechnology, Santa Cruz, Calif.). After the addition, the obtained solution was reacted at 4° C. for 1 hour. Thereafter, the beads were washed with a buffer (0.1% NP-40 and 50 mM tris-HCl adjusted pH 7.0) three times, followed by re-suspension in 15 µl of kinase buffer. Thus, a sample containing the beads to which the CDK of interest binds was yielded.

In the sample, all the CDK (hereinafter, if distinction is not necessary, simply called as "CDKs") including CDK itself, activated CDK to which cyclin binds, complexes of activated CDK and CDK inhibitor, and complexes of CDK and CDK inhibitor were bound to the antibodies, thereby fixing the CDKs to the beads. The activity of the CDKs in the sample was measured by the following measurement method.

Prepared was a substrate solution containing 5 mM adenosine 5'-O-(8-thiotriphosphate) (ATP-γS (Sigma)), a buffer solution (20 mM tris-HCl (pH:7.4), 0.1% Triton-X-100), and 10 µg of histone H1 (Upstate Biotechnology, Lake Placid, N.Y.) as a substrate for CDK1 and CDK2. The substrate solution was added to the sample containing the CDKs up to the total volume of 50 µl. The resulting sample solution was shaken for 10 minutes at 37° C. for incubation. As shown by the following formula, serine or threonine residue in the substrate was phosphorylated by the activated CDK, and monothiophosphorylated substrate was yielded.

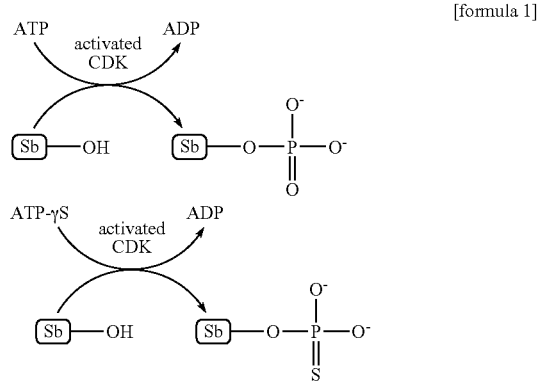

[formula 1]

The sample solution after the reaction was centrifuged at 1000 rpm for 10 seconds to precipitate the beads, and 30 µl of a supernatant containing monothiophosphates was obtained. 18 µl of the supernatant was mixed with 15 µl of a buffer solution containing 150 mM tris-HCl (pH: 9.2) and 5 mM EDTA, and 10 mM iodoacetyl fluorescein solution (100 mM tris-HCl (pH: 7.5) and 1 mM EDTA) was added. The obtained mixture was incubated in a dark place for 90 minutes at room temperature to label sulfur ions in the thiophosphates in the monothiophosphorylated substrate with fluorescence. The reaction of the iodoacetyl biotin with the thiophosphates was stopped by adding 6-mercaptoethanol.

0.4 µg of the fluorescence-labeled thiophosphorylated substrate was blotted on a PVDF membrane by using a slot blotter for adsorption. The blotted membrane was blocked with 1% of bovine serum albumin (BSA) for 30 minutes, followed by reaction with avidin-FITC (Vector, Burlingame, Calif.) at 37° C. for 1 hour. Thereafter, the membrane was washed with 50 mM TBS (25 mM tris-HCl (pH: 7.4) and 150 mM NaCl) for 10 minutes three times. After the washing, the image on the membrane was analyzed by a fluorescent image analyzer (Bio-Rad, Calif. U.S.A.). The activity of the CDKs was calculated based on a standard curve.

The standard curve was created by measuring activity of the activated CDK of interest in chronic myeloid leukemia cell K-562 with use of solutions with a variety concentrations of the only activated CDK.

Accordingly, 1U of the CDK activity to be measured is a value representing the amount having enzyme activity substantially equivalent to the enzyme activity with respect to 1 ng of total protein of K-562 cell. The enzyme activity corresponds to the amount of enzyme required for reacting a predetermined amount of a substrate.

[Measurement of Expression Level of CDK]

An initialized PVDF membrane (Millipore, Billerica, Mass.) obtained by immersing the membrane in TBS (25 mM tris-HCl (pH: 7.4) and 150 mM NaCl) was set to a well plate for slot blotter. Into each well (2×2×3 mm, allowable content: 100 µl) of the well-plate, and 50 µl of the cell lysate prepared based on the aforementioned method was seeded. The total amount of proteins contained in the cell lysate in each well was fallen in the range between 5 and 15 µg.

After seeding, each cell lysate was adsorbed onto the membrane by applying a negative pressure of about 200 mmHg from the bottom of the wells i.e. the backside of the membrane for about 15 seconds.

Then, a solution containing rabbit anti-CDK1-antibodies or rabbit anti-CDK2-antibodies, which is primary antibody capable of binding to the CDK of interest specifically, was seeded into each well, and the well plate was placed stationary at room temperature for about 30 minutes. Thereafter, the sample in the well was adsorbed onto the membrane from the bottom of the well with a negative pressure of 500 mmHg for about 50 seconds. Then, the membrane was washed with TBS (25 mM tris-HCl (pH: 7.4) and 150 mM NaCl).

Subsequently, a solution containing biotinylated anti-rabbit-antibodies (secondary antibody) was seeded into each well, and the well plate was placed stationary at room temperature for about 30 minutes. Then, the sample in the well was adsorbed onto the membrane from the bottom of the wells with a negative pressure of 500 mmHg for about 15 seconds. Thereafter, the membrane was washed with TBS (25 mM tris-HCl (pH: 7.4) and 150 mM NaCl).

Then, 40 µl of an FITC-labeled streptavidin reagent was seeded into each of the wells, and the well plate was placed stationary at room temperature for about 30 minutes to label the secondary antibody with the FITC. After the labeling, the sample in the well was adsorbed onto the membrane with a negative pressure of 500 mmHg for about 15 seconds. Thereafter, the membrane was washed with TBS (25 mM tris-HCl (pH: 7.4) and 150 mM NaCl).

After the PVDF membrane was removed from the well plate, the membrane was washed with distilled water, immersed in 20% methanol for 5 minutes, and then dried for about 15 minutes at room temperature. Thereafter, the fluorescent intensity of the protein adsorbed to the membrane was analyzed and measured by the image analyzer (Bio-Rad). The FIFC-labeled protein (CDK1 or CDK2) was quantified based on the previously created standard curve by converting the amount corresponding to the number of CDKs into the weight (ng) of the standard protein. The amount of CDKs measured by the above process is the total amount of the CDKs in the cells, such as CDK itself and CDK complexes (CDK-cyclin complex, CDK-cyclin-CDK inhibitor complex, CDK-CDK inhibitor complex, and complexes of CDK and other compounds).

The standard curve was created by seeding 50 µl each of solutions containing a purified recombinant CDK protein in five different concentrations in TBS containing 0.005% NP-40 and 50 µg/ml BSA into the wells which have been processed in the similar manner as mentioned above, labeling the protein with the FITC according to the similar manner as mentioned above, measuring the fluorescent intensity of the labeled protein, and expressing a relation between the fluorescent intensity of the labeled protein and the amount of the CDK protein.

[Calculations on Specific Activity of CDK]

The specific activity (mU/ng) of CDK was calculated based on the measured CDK activity and the measured expression level of CDK in accordance with the following equation.

$$CDK \text{ specific activity} = (CDK \text{ activity value})/(CDK \text{ expression level})$$

Example 1

Properties of Various Cancer Cell Lines

DNA contents and CDK specific activities were examined with respect to the cultured cells of the cell lines shown in Table 2 to know pathological properties of various cancer cells.

(1) DNA Content

After dispersion of cells of interest by treatment with trypsin/EDTA, and washing with PBS twice, the cells ($2 \times 10^5$ to $1 \times 10^6$) were collected by a centrifugal process of 100×g at 4° C. for 5 minutes. The collected cells were stirred by a vortex mixer, while gradually adding 1 ml of 70% ethanol precooled at −20° C. for cell fixation, followed by reaction at 4° C. or −20° C. for 2 hours or longer. After washing with PBS twice, 20 K unit/ml of RNase (Sigma), 50 µg/ml of propidium iodide (PI), and 1 mg/ml of glucose/PBS were added to sufficiently disperse the cells. Then, the cells were reacted at room temperature for 1 hour to fluorescently stain the DNA with PI. After the staining, solid components were removed with 35 mm nylon mesh (FALCON). Then, fluorescence measurement was conducted by FACScalibur (BD) at excitation wavelengths of 488/536 nm and 617 nm, and an analysis was conducted.

The measurement results are shown in FIGS. 2(a) through 2(h). Referring to FIGS. 2(a) through 2(h), the axes of ordinate represent the fluorescence intensity corresponding to the count i.e. the number of cells, and the axes of abscissas represents the DNA content.

Figure 3:
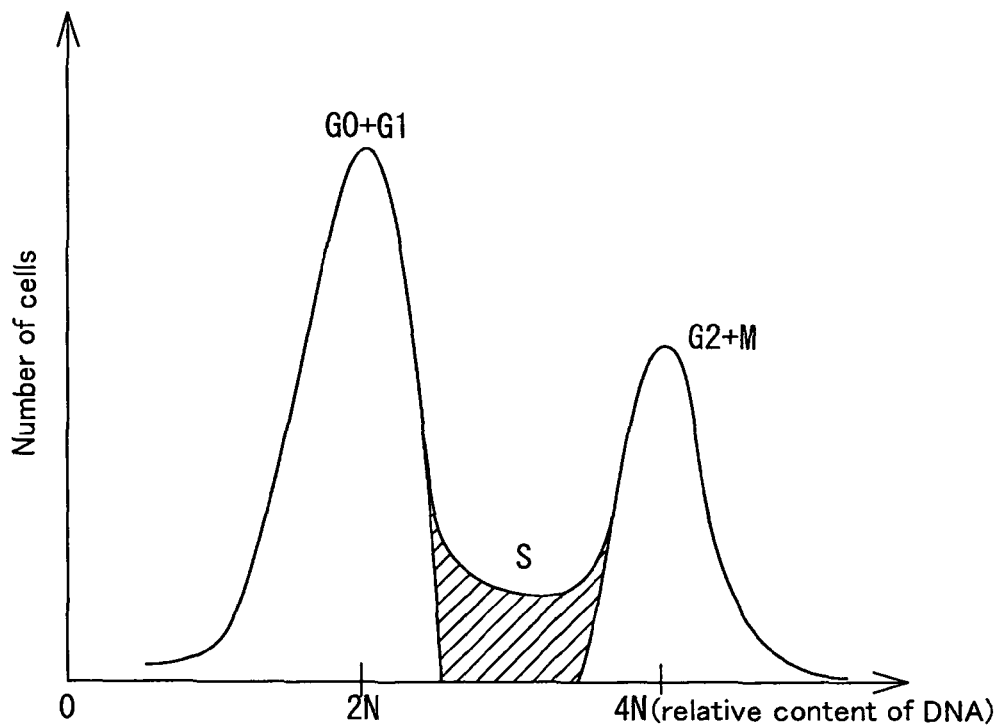
FIG. 3 is a graph for explaining results on DNA content data.
Figure 4:
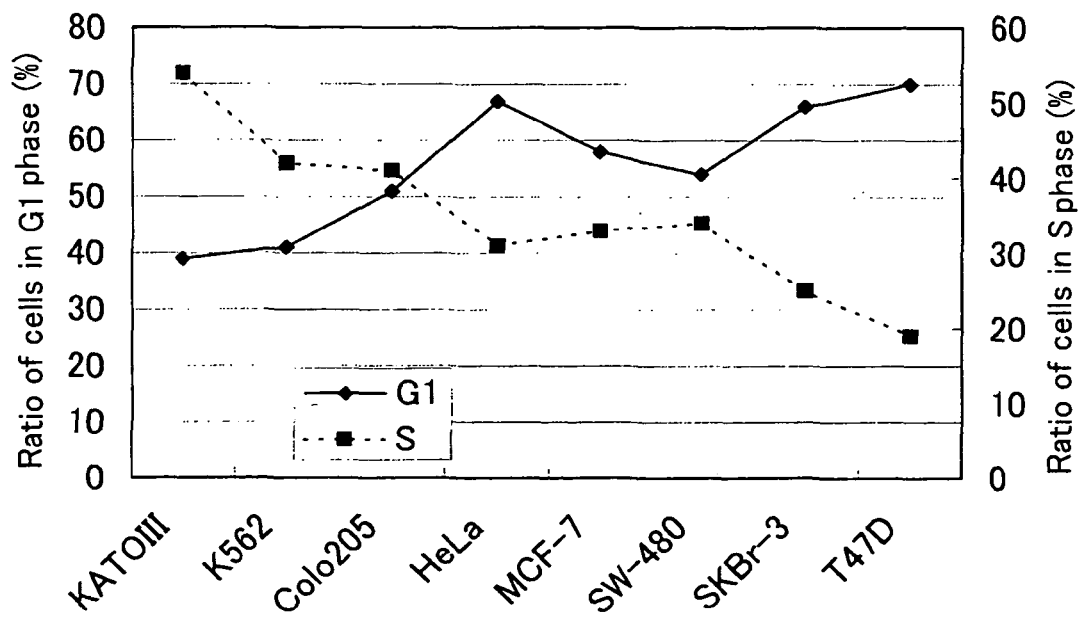
FIG. 4 is a graph showing ratios of cells in S phase with respect to various cell lines.

As shown in FIG. 3, generally, the relationship between the DNA content of animal cells and the number of cells is associated with the cell cycle. The ratio of cells in S phase and the ratio of cells in G1 phase were examined, using ModFit (Verity Software House) based on the measurement results in FIGS. 2(a) through 2(h). The examination results are shown in FIG. 4.

The results in FIGS. 2(a) through 2(h) and FIG. 4 show that the ratio of cells at S phase was large concerning KATOIII, K562, and Colo205 cell lines. Also, ploidy (particularly, aneuploidy) was observed concerning KATOIII, Colo205, and HeLa cell lines.

(2) CDK Specific Activity

Activities and expression levels of CDK1 and CDK2 were measured according to the aforementioned measurement method, with respect to cell lysates prepared based on the aforementioned preparation method, using the cultured cells shown in Table 2, and specific activities of CDK1 and CDK2 were obtained. The measurement results are shown in FIG. 5.

Figure 5:
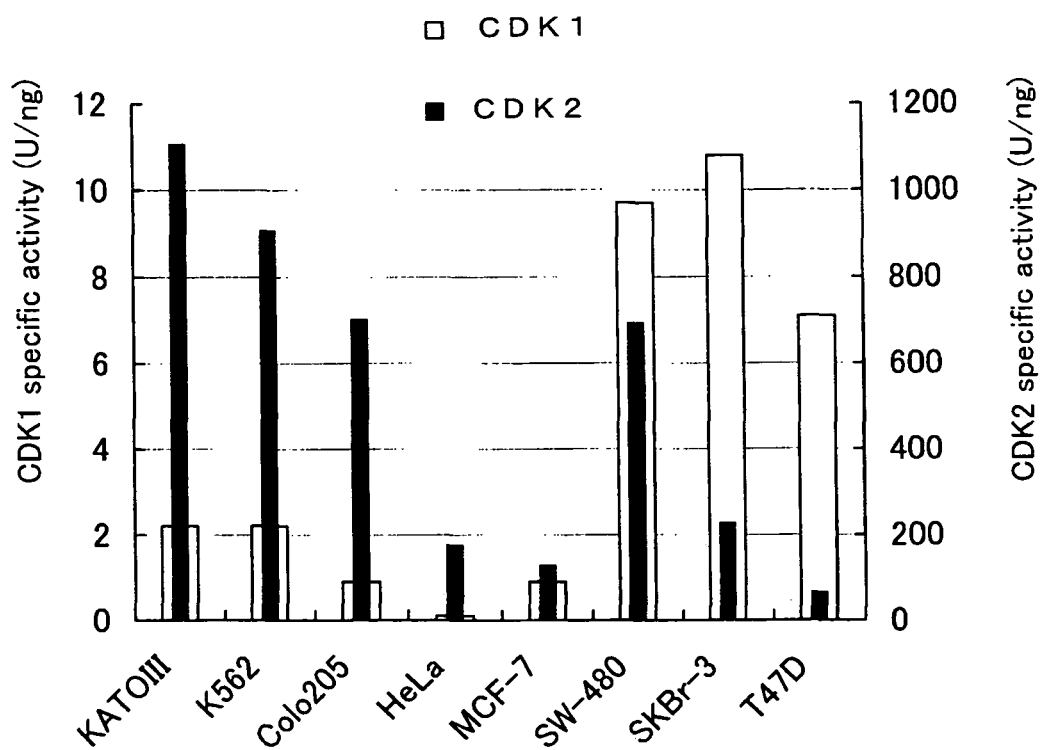
FIG. 5 is a graph showing measurement results on CDK1 specific activity and CDK2 specific activity of cells with respect to various cell lines.

Referring to FIG. 5, the thin solid black bars show specific activities of CDK2, the thick hollow bars show specific activities of CDK1, the left-side axis of ordinate shows a scale of specific activities of CDK1, and the right-side axis of ordinate shows a scale of specific activities of CDK2.

The cells examined are roughly classified into a group (KATOIII, K-562, Colo205, HeLa, and MCF-7 cells) where the specific activity of CKD1 is relatively low, and a group (SW480, SKBr3, and T47D) where the specific activity of CKD1 is relatively high, based on the magnitude of specific activity values of CKD1. It is clear that the magnitude of specific activity of CDK2 has a correlation to the ratio of cells at S phase, which is obtained based on the measurement of the DNA content. In other words, although the ratio of cells at S phase cannot be directly correlated to the magnitude of specific activity values of CDK2, the magnitude of specific activity value of CDK2 can be correlated to cell malignancy after the classification of the cells based on the specific activity values of CDK1.

Example 2

Correlation Between Assessment by Pathologists Concerning Biopsy Specimens and CDK Specific Activity Profile A relationship between relapse by a distant metastasis within 5 years after surgery, and a CDK specific activity profile based on the CDK1 specific activity and CDK2 specific activity which have been measured by the above method was examined with respect to cells obtained from biopsy specimens of actual cancer tissues.

(1) Assessment by Pathologists

Assessment results (TNM classification, lymph node metastasis condition, cancer tissue size, generation or non-generation of metastasis within 5 years after surgery, relapse site) by pathologists with respect to biopsy specimens (Nos. 1 through 77) obtained from actual 77 breast cancer patients are shown in Tables 3 and 4. All the 77 patients have an early stage breast cancer (Stage I or IIA).

In Table 3, "LN" indicates a condition of lymph node metastasis after surgery, wherein "a" means no metastasis was observed on regional lymph nodes, "b" means metastasis was observed on one to three regional lymph nodes, and "c" means metastasis was observed on four or more regional lymph nodes. "T" indicates the primary tumor size at the time of surgery, wherein "a" means the tumor size of 2 cm or smaller, "b" means the tumor size from 2 cm to 5 cm, and "c" means the tumor size of 5 cm or larger.

(2) Setting of Threshold Value

CDK1 specific activity and CDK2 specific activity were measured with respect to the cell lysates prepared based on the aforementioned method, using biopsy specimens obtained from 126 breast cancer patients. The obtained ratio values of CDK2 specific activity/CDK1 specific activity of the 126 cancer patients were ranked from the lowest value to the highest value, and a value capable of classifying the patients into two groups each consisting of 63 patients was set as a threshold value for the specific activity ratio. The threshold value was 46. The group where the ratio of CDK2 specific activity/CDK1 specific activity was smaller than the threshold value=46 was assessed to have a low relapse risk, and the group where the ratio of CDK2 specific activity/CDK1 specific activity was equal to or larger than the threshold value=46 was assessed to have a high relapse risk.

(3) Malignancy Grade Assessment by CDK Specific Activity Profiling

CDK1 specific activity and CDK2 specific activity were measured with respect to the cell lysates prepared based on the aforementioned method, using biopsy specimens obtained from 77 breast cancer patients. The 77 breast cancer patients were classified into a high risk group and a low risk group according to the threshold value set in (2). An assessment result by the specific activity profile is shown in Tables 3 and 4 along with the assessment result by pathologists.

Figure 6:
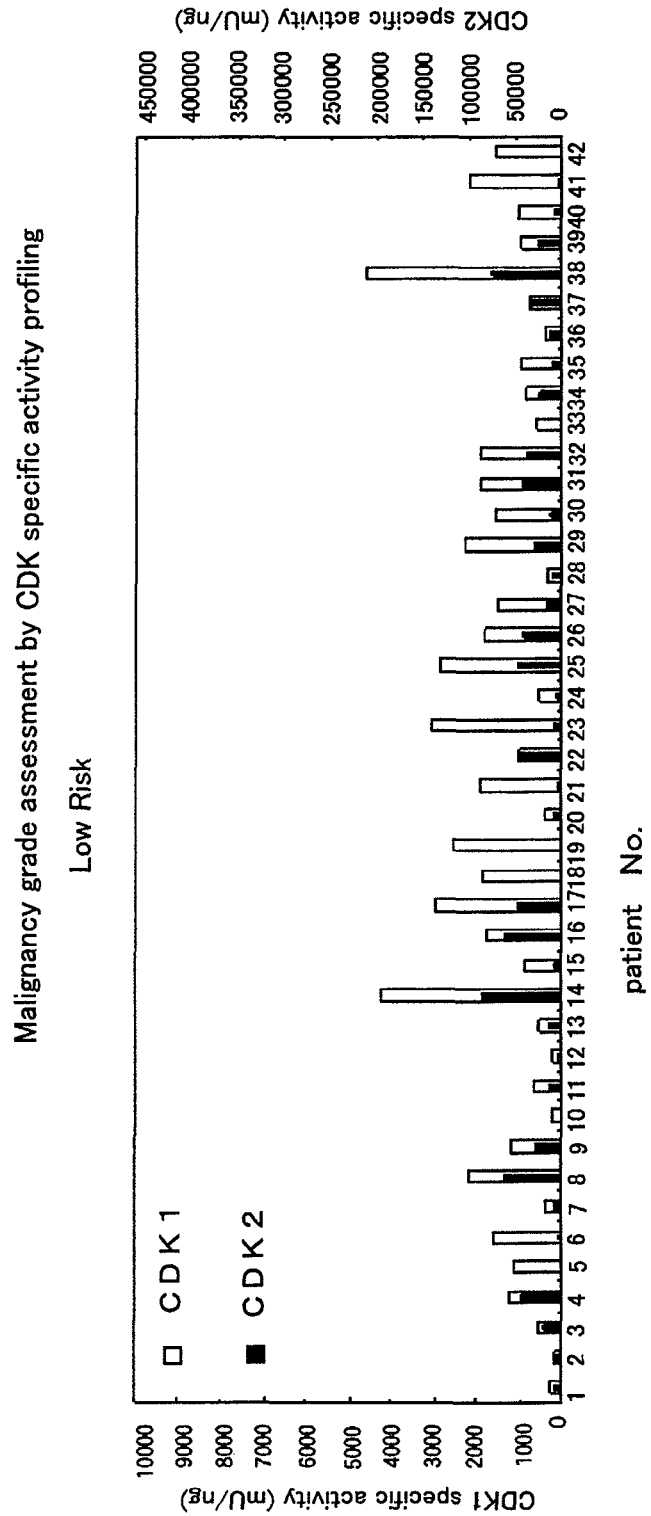
FIG. 6 is a diagram showing a CDK specific activity profile of specimens, which are assessed to have a low risk, out of tissues from breast cancer patients.
Figure 7:
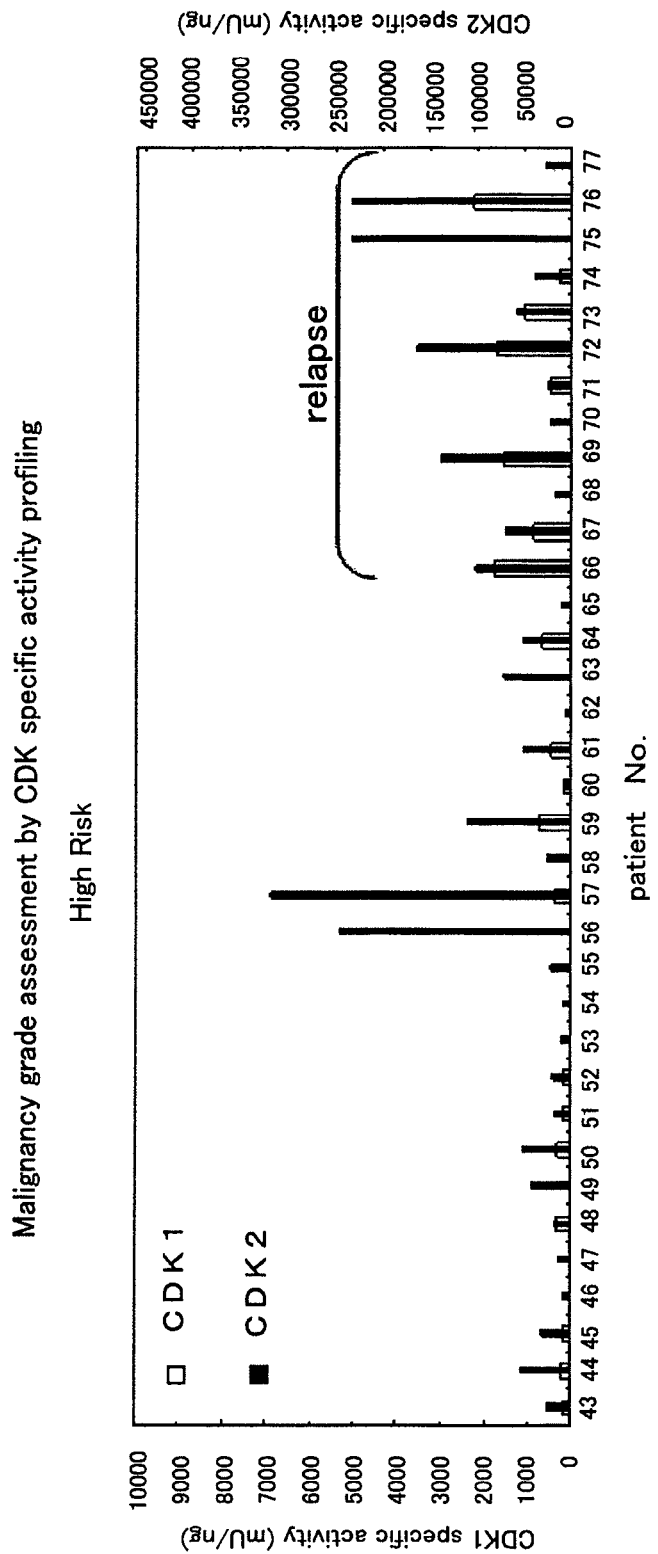
FIG. 7 is a diagram showing a CDK specific activity profile of specimens, which are assessed to have a high risk, out of tissues from breast cancer patients.

In creating a CDK specific activity profile graph having the axis of abscissas representing the respective patients, and the axes of ordinate representing the CDK1 specific activity and CDK2 specific activity, a graph showing a result on the CDK specific activity profile was created by setting the scale of the CDK2 specific activity by about 46 times as large as the CDK specific activity. The results on a CDK profile concerning the patient Nos. 1 through 42 who are assessed to belong to the low risk group are shown in FIG. 6, and the results on a CDK profile concerning the patient Nos. 43 through 77 who are assessed to belong to the high risk group are shown in FIG. 7.

TABLE 3

| Patient No | TNM | LM | T | relapse | Relapse site | Malignancy grade assessment |
|---|---|---|---|---|---|---|
| 1 | I | a | a | No | — | Low Risk |
| 2 | I | a | a | No | — | Low Risk |
| 3 | I | a | a | No | — | Low Risk |
| 4 | I | a | a | No | — | Low Risk |
| 5 | I | a | a | No | — | Low Risk |
| 6 | I | a | a | No | — | Low Risk |
| 7 | I | a | a | No | — | Low Risk |
| 8 | I | a | a | No | — | Low Risk |
| 9 | I | a | a | No | — | Low Risk |
| 10 | I | a | a | No | — | Low Risk |
| 11 | I | a | a | No | — | Low Risk |
| 12 | I | a | a | No | — | Low Risk |
| 13 | I | a | a | No | — | Low Risk |
| 14 | IIA | a | b | No | — | Low Risk |
| 15 | IIA | a | b | No | — | Low Risk |
| 16 | IIA | a | b | No | — | Low Risk |
| 17 | IIA | a | b | No | — | Low Risk |
| 18 | IIA | a | b | No | — | Low Risk |
| 19 | IIA | a | b | No | — | Low Risk |
| 20 | IIA | a | b | No | — | Low Risk |
| 21 | IIA | a | b | No | — | Low Risk |
| 22 | IIA | a | b | No | — | Low Risk |
| 23 | IIA | a | b | No | — | Low Risk |
| 24 | IIA | a | b | No | — | Low Risk |
| 25 | IIA | a | b | No | — | Low Risk |
| 26 | IIA | a | b | No | — | Low Risk |
| 27 | IIA | a | b | No | — | Low Risk |
| 28 | IIA | a | b | No | — | Low Risk |
| 29 | IIA | a | b | No | — | Low Risk |
| 30 | IIA | a | b | No | — | Low Risk |
| 31 | IIA | a | b | No | — | Low Risk |
| 32 | IIA | a | b | No | — | Low Risk |
| 33 | IIA | a | b | No | — | Low Risk |
| 34 | IIA | a | b | No | — | Low Risk |
| 35 | IIA | a | b | No | — | Low Risk |
| 36 | IIA | a | b | No | — | Low Risk |
| 37 | IIA | a | b | No | — | Low Risk |
| 38 | IIA | a | b | No | — | Low Risk |
| 39 | IIA | a | b | No | — | Low Risk |
| 40 | IIA | a | b | No | — | Low Risk |

TABLE 4

| Patient No | TNM | LN | T | relapse | Relapse site | Malignancy grade assessment |
|---|---|---|---|---|---|---|
| 41 | IIA | b | a | No | — | Low Risk |
| 42 | IIA | b | a | No | — | Low Risk |
| 43 | I | a | a | No | — | High Risk |
| 44 | I | a | a | No | — | High Risk |
| 45 | I | a | a | No | — | High Risk |
| 46 | IIA | a | b | No | — | High Risk |
| 47 | IIA | a | b | No | — | High Risk |
| 48 | IIA | a | b | No | — | High Risk |
| 49 | IIA | a | b | No | — | High Risk |
| 50 | IIA | a | b | No | — | High Risk |
| 51 | IIA | a | b | No | — | High Risk |
| 52 | IIA | a | b | No | — | High Risk |
| 53 | IIA | a | b | No | — | High Risk |
| 54 | IIA | a | b | No | — | High Risk |
| 55 | IIA | b | a | No | — | High Risk |
| 56 | IIA | a | b | No | — | High Risk |
| 57 | IIA | b | a | No | — | High Risk |
| 58 | IIA | a | b | No | — | High Risk |
| 59 | IIA | b | a | No | — | High Risk |
| 60 | IIA | b | a | No | — | High Risk |
| 61 | IIA | b | a | No | — | High Risk |
| 62 | IIA | b | a | No | — | High Risk |
| 63 | IIA | b | a | No | — | High Risk |
| 64 | IIA | b | a | No | — | High Risk |
| 65 | IIA | b | a | No | — | High Risk |
| 66 | I | a | a | Yes | Skin | High Risk |
| 67 | I | a | a | Yes | Lung | High Risk |
| 68 | IIA | a | b | Yes | Skin | High Risk |
| 69 | IIA | a | b | Yes | Lymph node | High Risk |
| 70 | IIA | a | b | Yes | Liver, bone | High Risk |
| 71 | IIA | a | b | Yes | Chest wall | High Risk |
| 72 | IIA | a | b | Yes | Lung | High Risk |
| 73 | IIA | a | b | Yes | Bone | High Risk |
| 74 | IIA | a | b | Yes | Skin | High Risk |
| 75 | IIA | a | b | Yes | Bone | High Risk |
| 76 | IIA | a | b | Yes | Lymph node | High Risk |
| 77 | IIA | a | b | Yes | Lung | High Risk |

As shown in Table 4, and FIGS. 6 and 7, 35 patients (Nos. 43 through 77) of the 77 early stage breast cancer patients who were assessed to have a relatively low malignancy were assessed to have a high risk in the CDK specific activity profiling, and relapse was observed in 12 patients (Nos. 66 through 77) among the 35 patients within 5 years after surgery. On the other hand, relapse was not observed for all the 42 patients who were assessed to have a low risk in the CDK specific activity profiling. It is obvious that the assessment result with a low CDK1 specific activity and a high CDK2 specific activity means high cancerous malignancy, and conversely, the assessment result with a low CDK2 specific activity and a high CDK1 specific activity means low cancerous malignancy, in the case where the tissue specimens from the breast cancer patients were profiled, considering the ratio of the CDK specific activities (in this example, the ratio of. CDK2 specific activity/CDK1 specific activity), in addition to the comparison result between the CKD1 specific activity value and the CKD2 specific activity value. In other words, it can be concluded that cancer cells from for instance, the patient No. 38 and No. 67 whose CDK1 specific activity is relatively high has a low malignancy, despite the CDK2 specific activity substantially as high as the CDK1 specific activity.

In other words, a cancer property and malignancy grade can be known based on a comparison result of the specific activity with the predetermined corresponding threshold value.

Example 3

Sensitivities to Anticancer Agent Docetaxel (1) Setting of Threshold Values and Criteria of Assessment The cell lysates for measurement were prepared based on the aforementioned method, using the cancer tissue specimens obtained from 1000 breast cancer patients before administration of taxan, although they have been treated with chemotherapy using anticancer agent taxan. Activities and expression levels of CDK1 and CDK2 were measured to calculate specific activities of CDK1 and CDK2, with respect to the cell lysates. On the other hand, these patients were classified into a group in which the tumor size reduction was observed and a group in which the tumor size reduction was not observed, as a result of chemotherapy using taxan. A threshold of the ratio of specific activities, i.e. the threshold of CDK2 specific activity/CDK1 specific activity, was set so that the threshold could serve the borderline between tumor size reduction group and no tumor size reduction group. The threshold value of the specific activity ratio was 16.

In the case that CDK1 specific activity value or CDK2 specific activity value is unduly large or unduly small, a threshold value was set so that the classification into the tumor size reduction group and no tumor size reduction group would be made based on either CDK1 specific activity or CDK2 specific activity. The threshold of CDK1 specific activity was 20, and the threshold of CDK2 specific activity was 500 and 10000.

The assessment was conducted as follows: comparing CDK1 specific activity and CDK2 specific activity with the corresponding threshold values respectively, and then, classifying into a sensitivity predicted group and a non-sensitivity predicted group, wherein a specimen having CDK1 specific activity of less than 20, i.e. CDK1 spepcific activity <20, and CDK2 specific activity of less than 500, i.e. CDK1 specific activity <500 was assessed as non-sensitivity predicted, while a specimen having CDK2 specific activity of more than 10000, i.e. CDK1 spepcific activity >10000 (sic. correctly CDK2 spepcific activity >10000) was assessed as sensitivity predicted. Thereafter, with respect to the specimens which have been classified into neither sensitivity group nor non-sensitivity group based on the aforementioned assessment, comparing the value of CDK2 specific activity/CDK1 specific activity with a corresponding threshold value=16, and carrying out assessment in which the specific activity ratio of 16 or more is assessed as sensitivity predicted, and the specific activity ratio of less than 16 is assessed as non-sensitivity predicted.

In Example 3, when CDK1 specific activity was 0, i.e. CDK1 specific activity value=0, and CDK2 specific activity fell in the range between 500 and 10000, i.e. 500≤CDK2 specific activity value ≤10000, the value of CDK2 specific activity/CDK1 specific activity was dealt as infinity for convenience of assessment. The specimen applied to such case was assessed as sensitivity predicted, because the ratio of specific activities was more than 16.

(2) CDK Specific Activity Profile and Sensitivity Prediction

Activities and expression levels of CDK1 and CDK2 were measured with respect to the cell lysates prepared based on the aforementioned method, using breast cancer tissue specimens obtained from breast cancer patients A through I who were not treated with a chemotherapy using an anticancer agent. Then, the specific activities of CDK1 and CDK2 were calculated.

Figure 8:
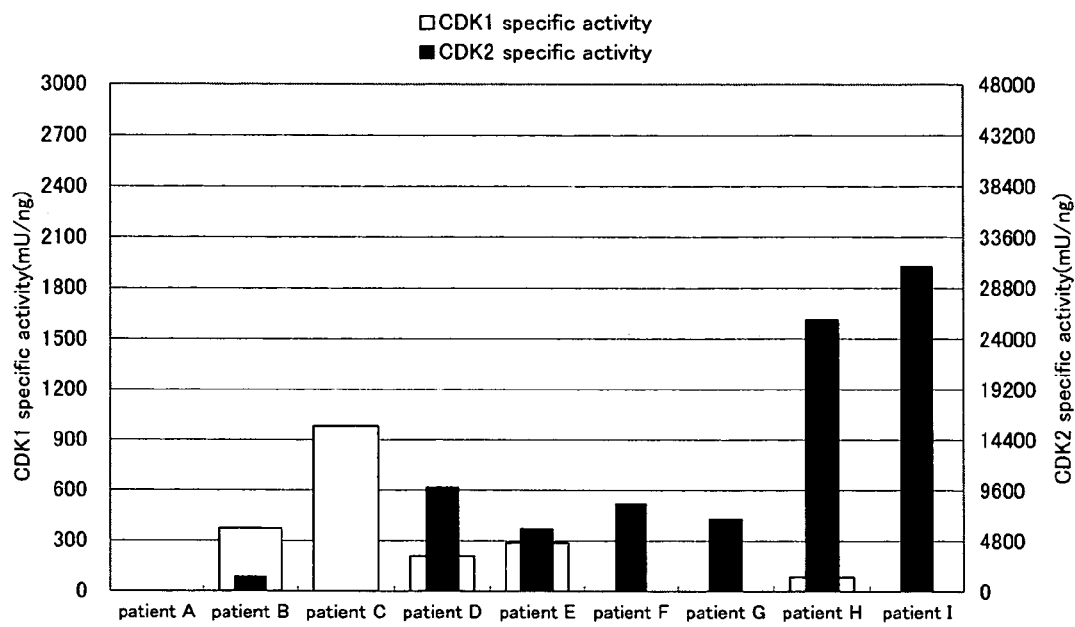
FIG. 8 is a graph showing measurement results on CDK1 specific activity and CDK2 specific activity in breast cancer patients A through I, wherein the patients A through I were administered with an anticancer agent docetaxel, and a change in tumor size after the administration was examined.

The patients were classified into a sensitivity predicted group and a non-sensitivity predicted group by comparing the CDK1 specific activity value, the CDK2 specific activity value, and the ratio of CDK2 specific activity/CDK1 specific activity with the respective corresponding threshold values set in (1) concerning the nine breast cancer patients A through I. FIG. 8 shows a CDK specific activity profile showing a relation of the patients A through I, which are expressed along the axis of abscissas, versus the CDK1 specific activity and the CDK2 specific activity, which are expressed along the axes of ordinate. The scale along the axis of ordinate concerning the CDK2 specific activity is 16 times as large as the scale of the axis of ordinate concerning the CDK1 specific activity.

The patients A through I were classified into a group who were predictably assessed to have sensitivity to docetaxel, and a group who were predictably assessed to have no sensitivity to docetaxel according to the aforementioned threshold value. The classification result is as follows.

docetaxel non-sensitivity predicted group: patients A, B, and C docetaxel sensitivity predicted group: patients D, E, F, G, H, and I (3) Chemotherapeutic Effects of Anticancer Agent Docetaxel An anticancer agent docetaxel (Aventis) was administered 4 times with an interval of 3 to 4 weeks, with 60 mg/M$^2$ (body surface area) per dosage for the breast cancer patients A through I. After the administration, the tumor size reduction was assessed.

A pathologist evaluated the tumors by palpation according to the criteria described in the following paper: Arbuck S G, Eisenhauer E A, Wanders J, Kaplan R S, Rubinstein L, Verweij J, Van Glabbeke M, van Oosterom A T, Christian M C, and Gwyther S G, "New guidelines to evaluate the response to treatment in solid tumors", J. Natl. Cancer Inst 2000; 92: 205-21. When the tumor was evaluated with the result of "Complete response" and "Partial response", the tumor was classified into the group of tumor size reduction. When the tumor was evaluated with the result of "Stable Disease" and "Progressive Disease", the tumor was classified into the group of non-tumor size reduction.

patients classified into non-tumor size reduction group: A, B, C, and D patients classified into tumor size reduction group: E, F, G, H, and I 8 out of the 9 patients showed matching between the predictive assessment result and the assessment result by the actual chemotherapy. Particularly, a positive predictive assessment results perfectly matched to an assessment result for the case where an actual chemotherapeutic effect was observed.

Example 4

Sensitivities to Anticancer Agent Paclitaxel (1) Setting of Threshold Value and Criteria of Assessment The threshold value and assessment criteria set in Example 3 were also adopted in Example 4.

(2) CDK Specific Activity Profile and Sensitivity Prediction

Activities and expression levels of CDK1 and CDK2 were measured with respect to the cell lysates prepared based on the aforementioned method, using breast cancer tissue specimens obtained from breast cancer patients J through P who has not been treated with a chemotherapy using an anticancer agent. Then, specific activities of CDK1 and CDK2 were calculated.

Figure 9:
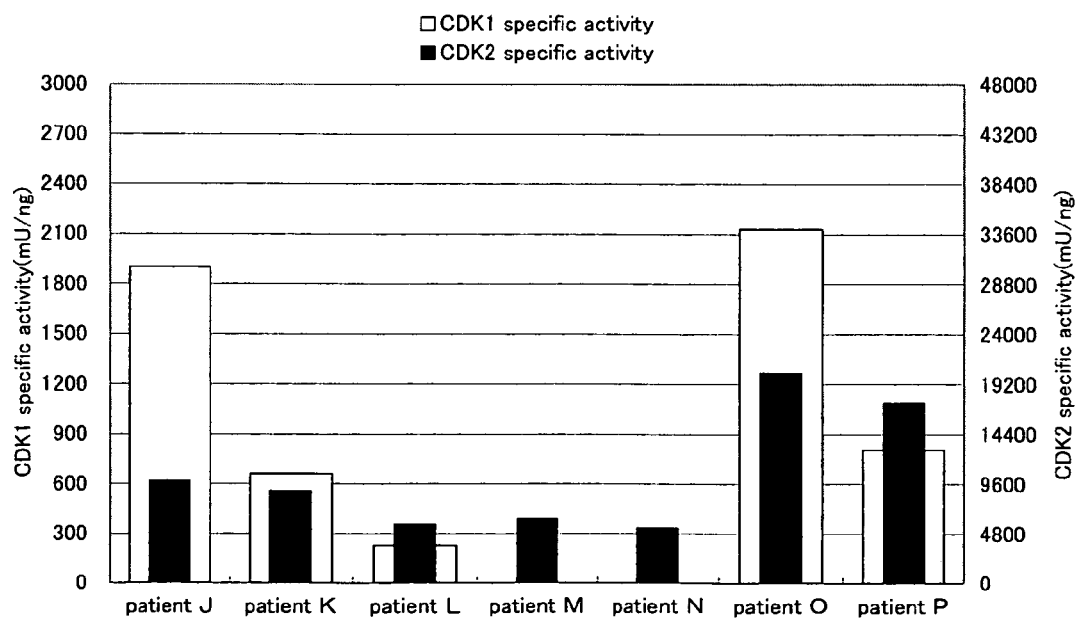
FIG. 9 is a graph showing measurement results on CDK1 specific activity and CDK2 specific activity in breast cancer patients J through P, wherein the patients J through P were administered with an anticancer agent paclitaxel, and a change in tumor size after the administration was examined.

Seven breast cancer patients, i.e. patients J through P, were classified into a sensitivity predicted group and a non-sensitivity predicted group by comparing the CDK1 specific activity value, the CDK2 specific activity value, and the ratio of CDK2 specific activity/CDK1 specific activity with the respective corresponding threshold values set in (1). FIGS. 9 shows a CDK specific activity profile showing a relation of the patients J through P, which are expressed along the axis of abscissas, versus the CDK1 activity and the CDK2 specific activity, which are expressed along the axes of ordinate. The scale along the axis of ordinate concerning the CDK2 specific activity is 16 times as large as the scale of the axis of ordinate concerning the CDK1 specific activity.

The patients J through P was classified into a group who were predictably assessed to have sensitivity to paclitaxel, and a group who were predictably assessed to have non-sensitivity to paclitaxel according to the aforementioned threshold value. The classification result is as follows:

paclitaxel non-sensitivity predicted group: patients J and K
paclitaxel sensitivity predicted group: patients L, M, N, O and P (3) Chemotherapeutic Effects of Anticancer Agent Paclitaxel An anticancer agent paclitaxel (Bristol Meyers Squibb) was administered once a week for 12 consecutive weeks, with 80 mg/$M^2$ (body surface area) per dosage for the breast cancer patients A through I (sic, correctly, J through P). After the administration, the tumor size reduction was assessed according to the same criterion as used in the administration of docetaxel.

The assessment results are as follows.

patients who were assessed that no tumor size reduction was observed: J
patients who were assessed that the tumor size reduction was observed: K, L, M, N, O, and P 7 out of the 8 patients showed matching (probability: 87.5%) between the predictive assessment result and the assessment result of the actual chemotherapy. 100% of patients positive assessed by the inventive method showed their tumor size reduction.

Exploitation In Industry

The assessment results based on the inventive assessment method, concerning cell properties, particularly, malignancy grade of cancer, have a high correlation to the assessment results by clinicians in medical institutes. Accordingly, the inventive method is useful for a definite diagnosis of diseases resulting from uncontrollable cell growth conditions such as cancers. Also, the inventive method can be applied to the study concerning uncontrollable growth conditions of various mammalian cells in addition to the study on human diseases.

Also, the inventive method of assessing sensitivity of animal cells to an irritant is useful as a method for examining whether various pharmaceutical agents and drugs such as anticancer agents, growth factors, or mutagens may affect cell growth. Particularly, the inventive method is useful in assessing effectiveness of pharmaceutical agents such as anticancer agents depending on the kind of cancer cells, or effectiveness of pharmaceutical agents such as anticancer agents resulting from a difference in individuals. Effectiveness of a chemotherapy using a selected anticancer agent can be predicted prior to actual administration of the anticancer agent to the patients. Accordingly, the inventive sensitivity assessment method can be used as a selection indicator for selecting a proper chemotherapy.

What is claimed is:

1. A method for judging a relapse risk of breast cancer, comprising:

measuring an activity value and expression level of CDK1 contained in a cancer tissue obtained from a breast cancer patient and an activity value and expression level of CDK2 contained in the cancer tissue;

obtaining a ratio of a CDK2 specific activity value versus a CDK1 specific activity value by the following expression:

the ratio =(the specific activity value of CDK2 contained in the cancer tissue/(the specific activity value of CDK1 contained in the cancer tissue) ={(the activity value of CDK2 contained in the cancer tissue)/(the expression level of CDK2 contained in the cancer tissue)}/{(the activity value of CDK1 contained in the cancer tissue)/(the expression level of CDK1 contained in the cancer tissue)};

comparing the obtained ratio with a threshold value; and wherein the threshold value is determined by ranking ratio values of CDK2 specific activity values versus CDK1 specific activity values from a population of breast cancer patients, from lowest value to highest value, and setting a median value classifying the breast cancer patients into a low relapse group and a high relapse group as the threshold value; and judging high relapse risk when the obtained ratio is equal to or higher than the threshold value.

2. The method for judging according to claim 1, further comprising a step of diagnosing a malignancy grade of the cancer tissue obtained from the breast cancer patient on the basis of the judging step.

3. The method for judging according to claim 1, wherein the expression level of CDK1 is measured by using an anti-CDK1 antibody and the expression level of CDK2 is measured by using an anti-CDK2 antibody.

4. The method for judging according to claim 3, wherein the expression level of CDK1 is measured by lysing the cancer tissue with a buffer solution, detecting CDK1 contained in the obtained lysate by the anti-CDK1 antibody, and obtaining an amount of the detected CDK1 by the anti-CDK1 antibody; and wherein the expression level of CDK2 is measured by lysing the cancer tissue with a buffer solution, detecting CDK2 contained in the obtained lysate by the anti-CDK2 antibody, and obtaining an amount of the detected CDK1 by the anti-CDK2 antibody.

5. The method for judging according to claim 1, wherein the activity value of CDK1 is measured by lysing the cancer tissue with a buffer solution, detecting CDK1 contained in the obtained lysate with an anti-CDK1 antibody, and obtaining the amount of activity value CDK1 with a substrate solution containing a substrate for CDK1 and adenosine 5'-0-(8-thiotriphosphate); and wherein the activity value of CDK2 is measured by lysing the cancer tissue with a buffer solution, detecting CDK2 contained in the obtained lysate with an anti-CDK2 antibody, and obtaining the amount of activity value CDK2 with a substrate solution containing a substrate for CDK2 and adenosine 5'-0-(8-thiotriphosphate).

6. The method for judging according to claim 5, wherein the substrate for CDK1 and the substrate for CDK2 are histone H1.

7. The method for judging according to claim 1, wherein the cancer tissue is a biopsy specimen obtained from the breast cancer patient.

* * * * *